(12) United States Patent
Marker (10) Patent No.: US 8,573,074 B1
(45) Date of Patent: Nov. 5, 2013

(54) VEHICLE MOUNTED SOIL SAMPLER

(76) Inventor: Ronald Marker, Akron, MI (US)

( * ) Notice: Subject to any disclaimer, the term of this patent is extended or adjusted under 35 U.S.C. 154(b) by 221 days.

(21) Appl. No.: 13/241,151

(22) Filed: Sep. 22, 2011

(51) Int. Cl.
*G01N 1/04* (2006.01)

(52) U.S. Cl.
USPC ............... 73/864.45; 73/864.41; 73/864.44

(58) Field of Classification Search
USPC ............... 73/864.45, 864.32, 864.41, 864.44; 173/19, 24, 25; 175/20
See application file for complete search history.

(56) References Cited

U.S. PATENT DOCUMENTS

| | | | | |
|---|---|---|---|---|
| 3,084,553 A | * | 4/1963 | Cullinan et al. | 73/864.31 |
| 3,224,512 A | * | 12/1965 | Alexander | 173/19 |
| 3,331,249 A | * | 7/1967 | Boxrud | 73/864.31 |
| 3,464,504 A | * | 9/1969 | Stange | 173/28 |
| 3,593,809 A | * | 7/1971 | Derry | 175/51 |
| 3,625,296 A | * | 12/1971 | Mabry et al. | 173/24 |
| 4,191,263 A | * | 3/1980 | Malterer | 173/28 |
| 4,316,393 A | * | 2/1982 | Philipenko | 73/864.45 |
| RE30,901 E | * | 4/1982 | Boxrud | 73/864.31 |
| 4,332,301 A | * | 6/1982 | Jonell | 175/50 |
| 4,333,541 A | * | 6/1982 | Doty | 175/162 |
| 4,482,021 A | * | 11/1984 | Repski | 175/209 |
| 4,534,231 A | * | 8/1985 | Jonsson et al. | 73/864.43 |
| 4,685,339 A | * | 8/1987 | Philipenko | 73/864.45 |
| 4,989,678 A | * | 2/1991 | Thompson | 175/20 |
| 5,076,372 A | * | 12/1991 | Hellbusch | 175/20 |
| 5,211,248 A | * | 5/1993 | Nosewicz et al. | 175/20 |
| 5,394,949 A | * | 3/1995 | Wright et al. | 175/20 |
| 5,435,399 A | * | 7/1995 | Peterson et al. | 175/20 |
| 5,741,983 A | * | 4/1998 | Skotnikov et al. | 73/864.45 |
| 5,887,491 A | * | 3/1999 | Monson et al. | 73/864.74 |
| 5,950,741 A | * | 9/1999 | Wright et al. | 175/20 |
| 6,016,713 A | * | 1/2000 | Hale | 73/864.45 |
| 6,237,429 B1 | * | 5/2001 | Melnyk | 73/864.45 |
| 6,260,633 B1 | * | 7/2001 | Machek et al. | 175/20 |
| 6,360,829 B1 | * | 3/2002 | Naber et al. | 175/20 |
| 6,363,803 B1 | * | 4/2002 | Hubers | 73/864.43 |
| 6,766,865 B1 | * | 7/2004 | Dagel et al. | 172/22 |
| 6,769,317 B1 | * | 8/2004 | Hamilton et al. | 73/864.44 |
| 6,959,245 B2 | * | 10/2005 | Rooney et al. | 702/5 |
| 7,255,016 B2 | * | 8/2007 | Burton | 73/864.45 |
| 7,677,119 B2 | * | 3/2010 | Garel | 73/864.45 |
| 7,836,972 B2 | * | 11/2010 | Pavlik | 175/20 |
| 2005/0172733 A1 | * | 8/2005 | Drummond et al. | 73/864.41 |

* cited by examiner

*Primary Examiner* — David A Rogers
(74) *Attorney, Agent, or Firm* — Robert L. Farris; Farris Law, P.C.

(57) ABSTRACT

The vehicle mounted soil sampler includes a vertical mast tube connected to a receiver hitch mounted on a vehicle. A support plate is clamped to the mast. A drive shaft and gear, driven by a motor, is journaled in a gear housing mounted on the support plate. An elongated gear rack is parallel to the vertical mast and moved vertically by the drive shaft and gear in the gear housing. A tubular soil probe with an open bottom end and an open slot is attached to the gear rack. A spoon bar is pivotally attached to the mast tube. A spoon bar lower end is urged into the open slot and removes soil from the tubular soil probe during upward movement of the gear rack. A soil sample container catches soil discharged from the soil probe. A plastic guide bearing guides the gear rack.

18 Claims, 7 Drawing Sheets

VEHICLE MOUNTED SOIL SAMPLER

CROSS REFERENCE TO RELATED APPLICATION

Technical Field

The vehicle mounted soils sampler includes a soil probe mounted on a vehicle, for vertical movement into an agricultural field, which is driven down into the soil to obtain a soil sample, raised to lift the soil sample from the field, and deposits the soil sample in a soil collector for soil analysis.

BACKGROUND OF THE INVENTION

Farmers have in the past taken soil samples in a few selected positions in a farm field. The soil samples were analyzed to determine what plant nutrients were lower than desired for the next crop and to determine the effective hydrogen-ion concentration (pH). Chemicals were then applied to the entire field based on a few soil samples. The application of chemicals was based on an assumption that the same chemicals were needed in the entire field. Sometimes it was assumed that other fields in the same general area needed the same additives without analysis of soil samples from each of these other fields.

Many of the chemicals applied to fields today such as ammonia are made from hydrocarbons. Hydrocarbons and other chemicals based on oil are relatively expensive and will most likely become more expensive in coming years. Farmers have also learned that many chemical additives will damage crops if the concentrations are too high. A significant expense is incurred each time a chemical is applied as a liquid, a gas, a powder or as granular solids. These expenses can be reduced by applying chemicals at the same time other activities such as tillage, planting, row crop cultivation, or crop harvesting occur. However, some chemicals need to be applied when none of the above activities are appropriate.

Harvesting machines are often equipped with global positioning systems and sensors that measure crop yield, moisture content, protein content, and other factors that may be of interest. Chemical applicators with global positioning systems and application controls connected to an application controller are commercially available. These computer controlled applicators can control chemical application rates to apply the desired application rate throughout the entire area of a field and to substantially eliminate excessive chemical application in all areas of a field.

Determining the quantity of each chemical that needs to be applied to each part of a field is based on soil samples, past crop production data, and the requirements of the next crop to be planted in the field. To obtain the best data to determine the quantity of each chemical to be applied, a substantial number of soil samples taken in a predetermined distribution throughout the field need to be taken. Each soil sample obtained is identified by the location in which it was taken and the date on which the sample was obtained. The date of the sample is important because the measured quantities can change over time. Volatile chemicals may evaporate over time for example. The number of soil samples that can be obtained in a given period of time is limited by the apparatus employed to obtain each soil sample.

SUMMARY OF THE INVENTION

The vehicle mounted soil sampler includes a generally vertical mast tube with a rectangular cross section. A hitch mount assembly includes a hitch plate clamped to the generally vertical mast tube. The hitch plate is vertically adjustable relative to the generally vertical mast. A hitch bar is fixed to the hitch plate. The hitch bar is telescopically receivable in a receiver hitch mounted on a vehicle. A receiver hitch pin passes through a horizontal bore through the receiver hitch and a horizontal bore through the hitch bar to hold the hitch bar in the receiver hitch tube.

A support plate is clamped to the generally vertical mast. The support plate is vertically adjustable relative to the generally vertical mast tube.

A motor is connected to a gear box, a gear box output shaft, a shaft coupler, and a drive shaft and gear journaled in a gear housing. The motor and the gear housing are both clamped to the support plate.

An elongated gear rack with gear teeth is held substantially parallel to the generally vertical mast by the gear housing. The elongated gear rack is movable parallel to the generally vertical mast by the motor connected to the drive shaft and gear journaled in the gear housing. The elongated gear rack is movable in a downward direction. The motor, drive shaft and gear journaled in the gear housing are reversible to move the elongated gear rack generally parallel to the generally vertical mast in an upward direction.

At least one rack guide bearing is attached to the support plate above the gear housing. The at least one rack guide bearing is engageable with the elongated gear rack to limit movement of the elongated gear rack away from the drive shaft and gear journaled in the gear housing. The at least one guide bearing is also engageable with a first rack side and a second rack side. An idler gear is journaled on the support plate and engageable with the gear teeth on the elongated gear rack adjacent to the at least one guide bearing and above the gear housing. The idler gear limits movement of the elongated gear rack away from the at least one guide bearing.

A tubular soil probe has a probe upper end clamped to a bottom end of the elongated gear rack and a soil probe open end. The soil probe open end permits movement of soil into the interior of the soil probe upon downward movement of the soil probe driven by the elongated gear rack, the drive shaft and gear journaled in the gear housing and the motor. The tubular soil probe also has an open slot.

A spoon bar is pivotally attached to a spoon mounting plate clamped to the generally vertical mast, by a horizontal pivot pin. The spoon bar includes a bar lower portion with a concave surface. The bar lower portion with the concave surface is movable into and out of the open slot in the tubular soil probe upon pivotable movement about the horizontal pivot pin. A spring urges the bar lower portion of the spoon bar toward the open slot. A soil sample container is supported by the generally vertical mast in a position to catch soil samples moved through the open slot of the tubular soil probe in response to upward movement of the soil probe and the elongated gear rack.

The vehicle mounted soil sampler includes an upper lock nut on a threaded stud that engages an elongated gear rack bottom end and holds the upper locknut and threaded stud from rotating relative to the elongated gear rack. A lower lock nut on the threaded stud engages the tubular soil probe, after the tubular soil probe is screwed onto the threaded stud, and holds the tubular soil probe in a selected position with the open slot in the tubular soil probe positioned to receive the bar lower portion of the spoon bar.

A lower limit switch trigger is mounted on the elongated gear rack and activates a lower limit switch to limit upward movement of the elongated gear rack. An upper limit switch trigger is mounted on the elongated gear rack. An upper limit switch is activated by the upper limit switch trigger to limit downward movement of the elongated gear rack. The upper limit switch trigger is movable to different positions on the elongated gear rack.

BRIEF DESCRIPTION OF DRAWINGS

The presently preferred embodiment of the invention is disclosed in the following description and in the following drawings, wherein.

DETAILED DESCRIPTION OF THE PREFERRED EMBODIMENTS

The vehicle mounted soil sampler 10 includes a generally vertical mast 12. The generally vertical mast 12 is a metal tube 14. The metal tube 14 is preferably a light weight metal such as aluminum or titanium.

Figure 2:
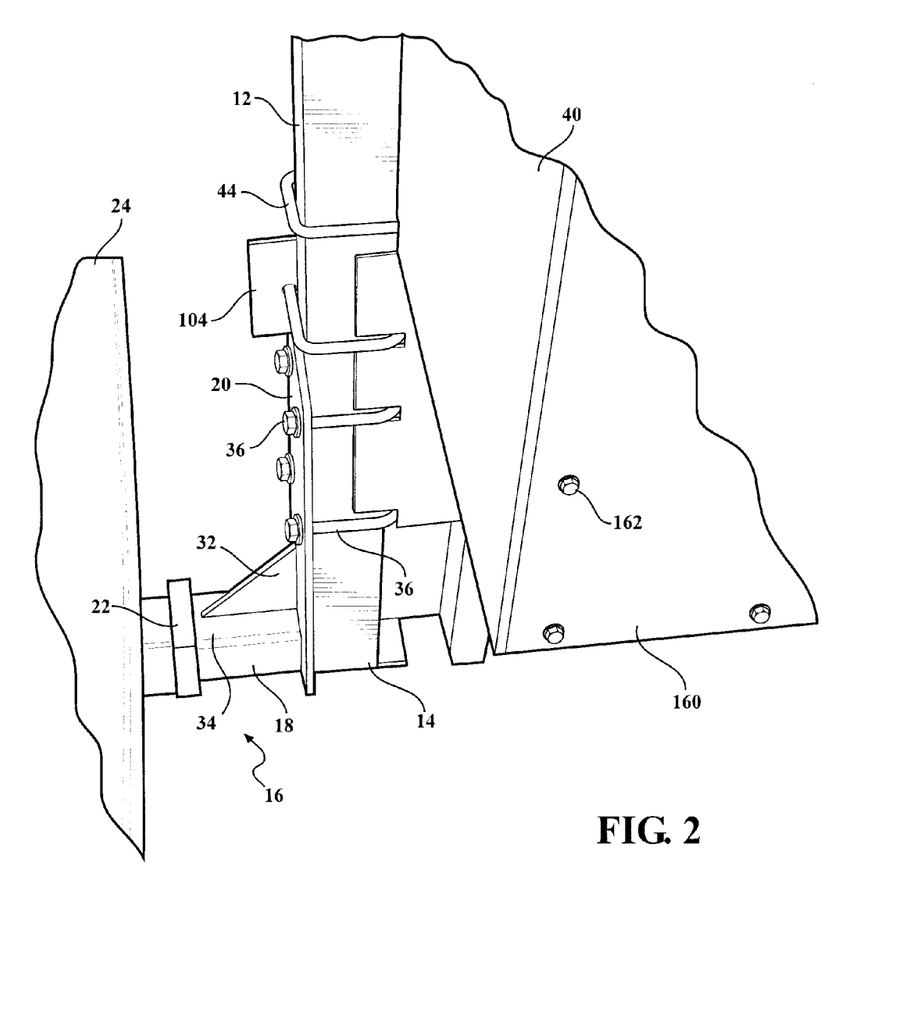
FIG. 2 is a perspective view of the mounting structure connecting the soil sampler to a utility vehicle with parts broken away.

A hitch mount assembly 16, as shown in FIG. 2, includes a steel hitch tube 18 and a steel plate 20. The hitch tube 18 is sized to be telescopically received in a receiver hitch 22 mounted on a vehicle 24. The receiver hitch 22 may be on the front, side or rear of the vehicle 24. A retainer pin, not shown, passes through a bore through the receiver hitch 22 and through a bore through the hitch tube 18. The bore through the hitch tube 18 is horizontal. Multiple bores can be provided in the hitch tube 18 if desired to accommodate different positions of the receiver hitch 22 relative to a vehicle 24 and to adjust the distance between the soil sampler 10 and portions of the vehicle. The steel plate 20 of the hitch mount assembly 16 is welded to an end 30 of the hitch tube 18. As shown in the Figures, the steel plate 20 extends vertically upward from the hitch tube 18. A gusset 32 is welded to the steel plate 20 and the top surface 34 of the hitch tube 18.

U-bolts 36 clamp the tube 14 of the mast 12 to the steel plate 20 of the hitch mount assembly 16. The U-bolts 36 permit vertical adjustment of the vertical mast 12 relative to the hitch tube 18. Receiver hitches 22 vary in height depending upon the vehicle 24 to which receiver hitch is attached. The receiver hitch 22 on a small passenger van, for example, may be close to the ground and require raising of the mast 12, relative to the hitch mount assembly 16, to obtain sufficient ground clearance during movement to a site where a soil sample is to be obtained. A receiver hitch 22 on high clearance vehicle such as a four wheel drive truck may be above the ground a substantial distance. With a high receiver hitch, it may be necessary to lower the mast 12 relative to hitch mount assembly 16. With a very high receiver hitch 22, it may be necessary to rotate the hitch mount assembly 16 so that the steel plate 20 extends downwardly from the hitch tube 18.

Figure 3:
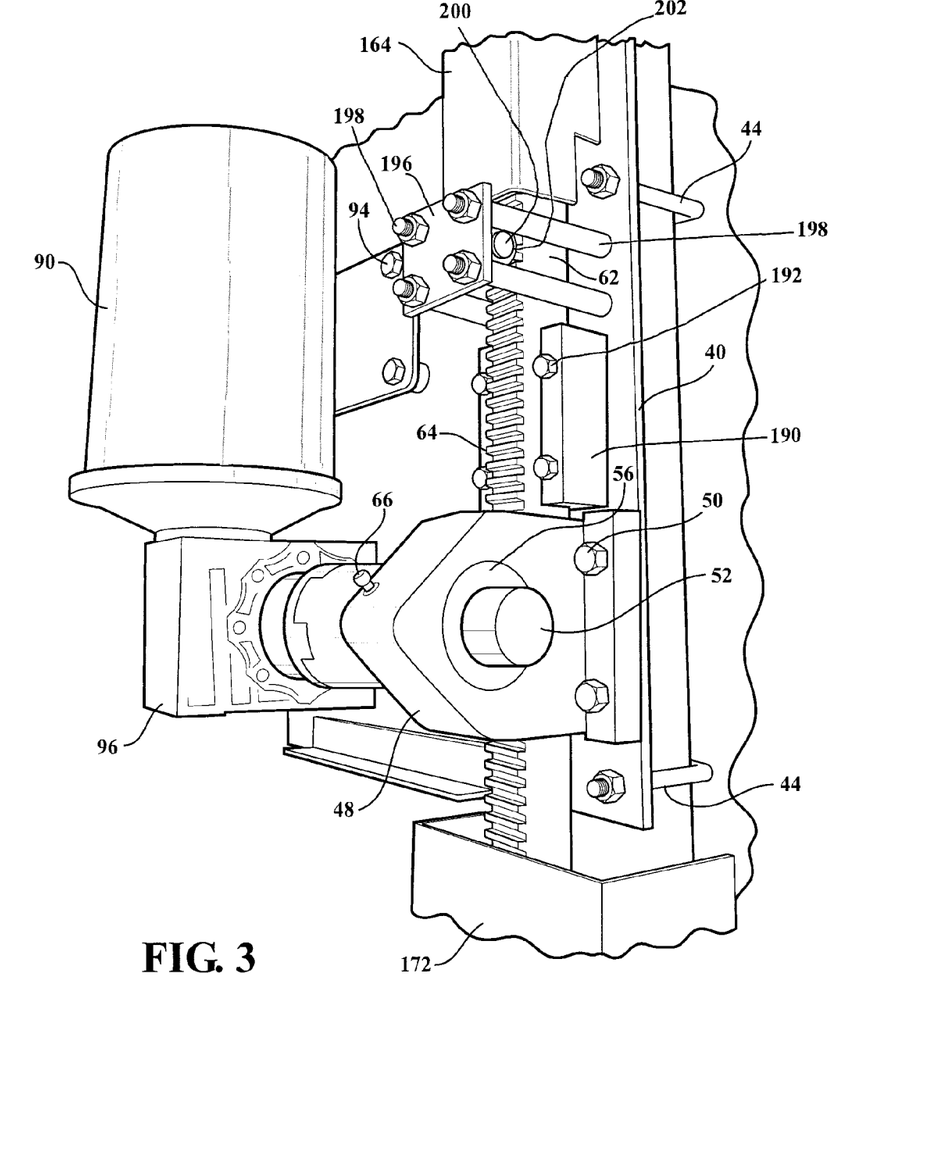
FIG. 3 is a perspective view of the mounting structure connecting to a utility vehicle with parts broken away.
Figure 4:
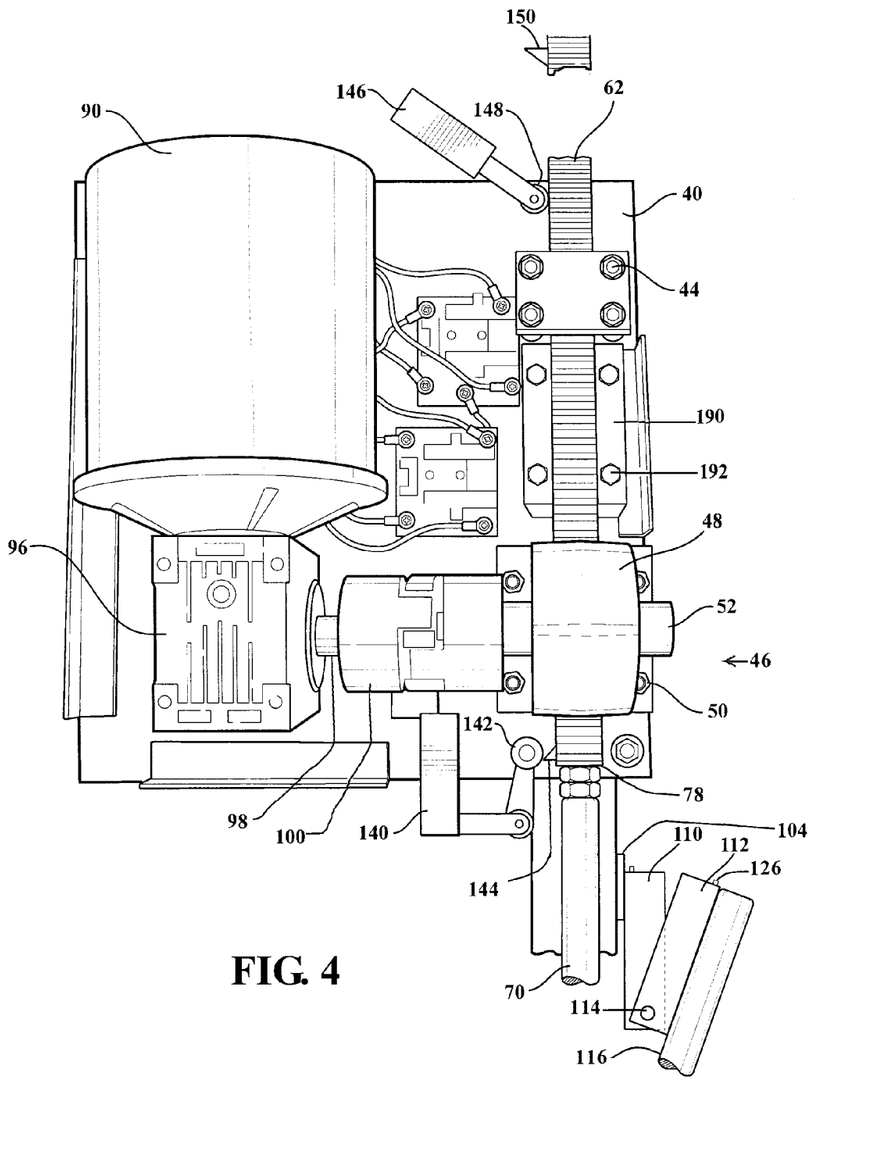
FIG. 4 is a rear elevational view of the soil sampler drive with parts broken away.
Figure 5:
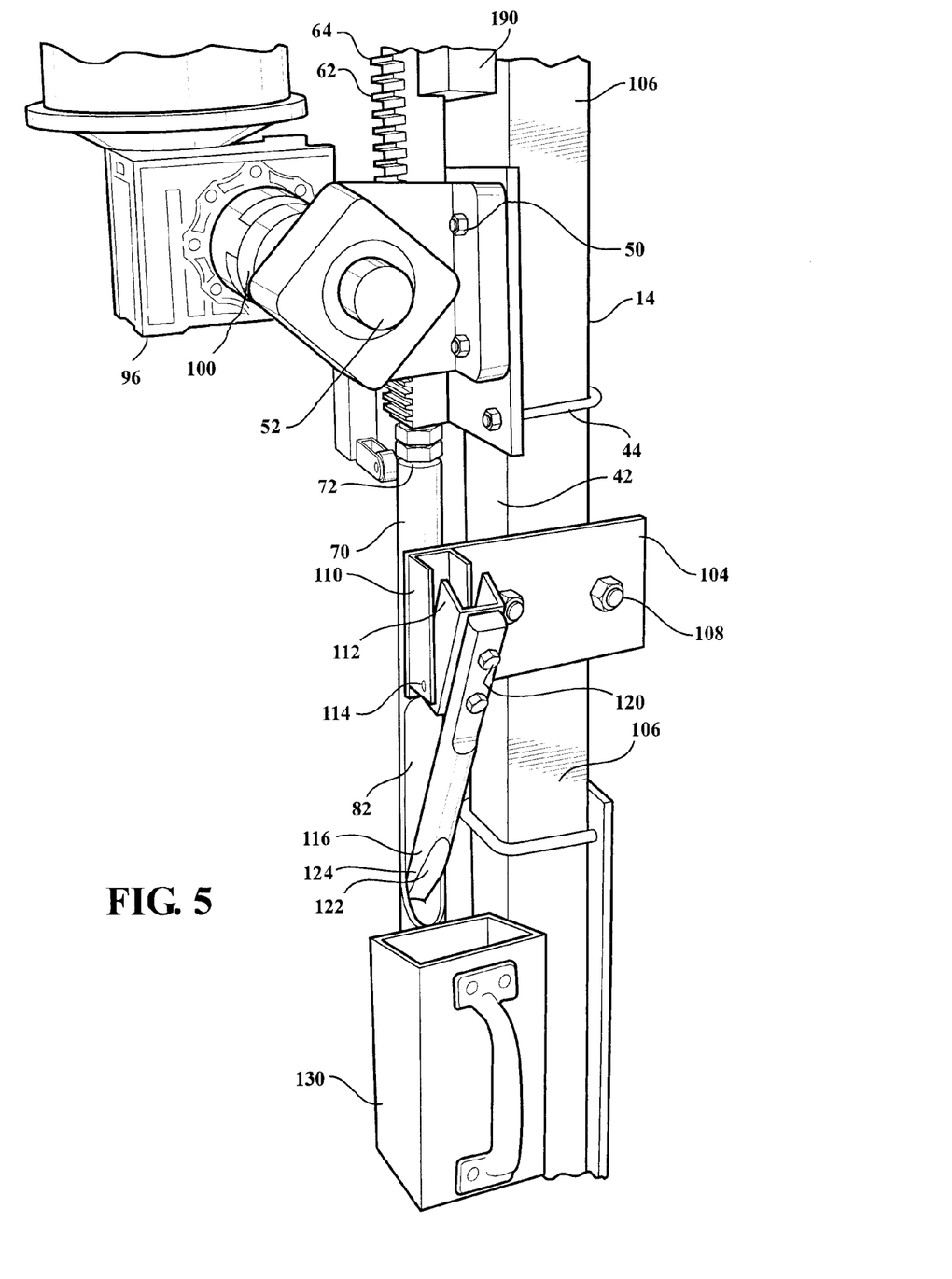
FIG. 5 is a right side elevational view of the soil sampler drive and spoon assembly.

A motor support plate 40, as shown in FIGS. 3 and 4, is clamped to a rearward facing surface 42 on the tube 14 of the vertical mast 12, by U-bolts 44. A rack drive assembly 46 with a housing 48 is clamped to the motor support plate 40 by bolts 50. A rack drive shaft 52 is journaled in the housing 48 by bearings 54 and 56. A spur gear is fixed to the rack drive shaft 52 between the bearings 54 and 56 inside the housing 48. An elongated steel gear rack 62 has gear teeth 64 that mesh with the spur gear and passes between the spur gear and the motor support plate 40. The gear rack 62 is spaced from the rearward facing surface 42 on the tube 14 and is generally parallel to the rearward facing surface. The gear teeth 64 extend away from the tube 14. A grease fitting 66 is provided in the housing 48 for lubrication of the bearings 54 and 56.

A tubular soil probe 70 has an upper end 72 with a threaded bore that screws onto a vertical threaded stud extending from the bottom end 78 of the gear rack 62. The tubular soil probe 70 has an open end 80 that receives soil samples and an open side slot 82 for extraction of soil samples.

An electric motor 90 with a vertical output shaft is clamped to the motor support plate 40 by bolts 94. A ninety degree gear box 96 is driven by the vertical motor output shaft. A horizontal gear box output shaft 98 is nearly coaxial with the rack drive shaft 52 and is connected to the rack drive shaft by a shaft coupler 100.

A spoon assembly 102, shown in FIG. 4, for removing soil samples from the tubular soil probe 70, includes a spoon mounting plate 104 clamped to a right side surface 106 of the metal tube 14 by a U-bolt 108. A fixed channel member 110 is attached to the spoon mounting plate 104. A pivoted channel member 112 is pivotally attached to the fixed channel member 110 by a pivot pin 114. The pivot pin 114 has a substantially horizontal pivot axis. A spoon bar 116 is clamped to the pivoted channel member 112 by bolts 120. The spoon bar 116 has a concave surface 122 on the lower portion 124. A torsion spring 126 mounted on the pivot pin 114 urges the lower portion 124 of the spoon bar 116 toward the soil probe 70. When the soil probe 70 is filled with a soil sample and raised, the torsion spring 126 urges the lower portion 124 of the spoon bar 116 toward the soil probe 70 and into the open side slot 82. The concave surface 122 on the lower portion 124 of the spoon bar 116 engages the soil sample and urges the soil sample out of the tubular soil probe 70 through the open side slot 82. A soil sample container 130 catches the soil sample extracted from the soil probe 70 by the concave surface 122. Lowering the soil probe 70 to obtain another soil sample cams the soil probe out of the open side slot 82.

Figure 1:
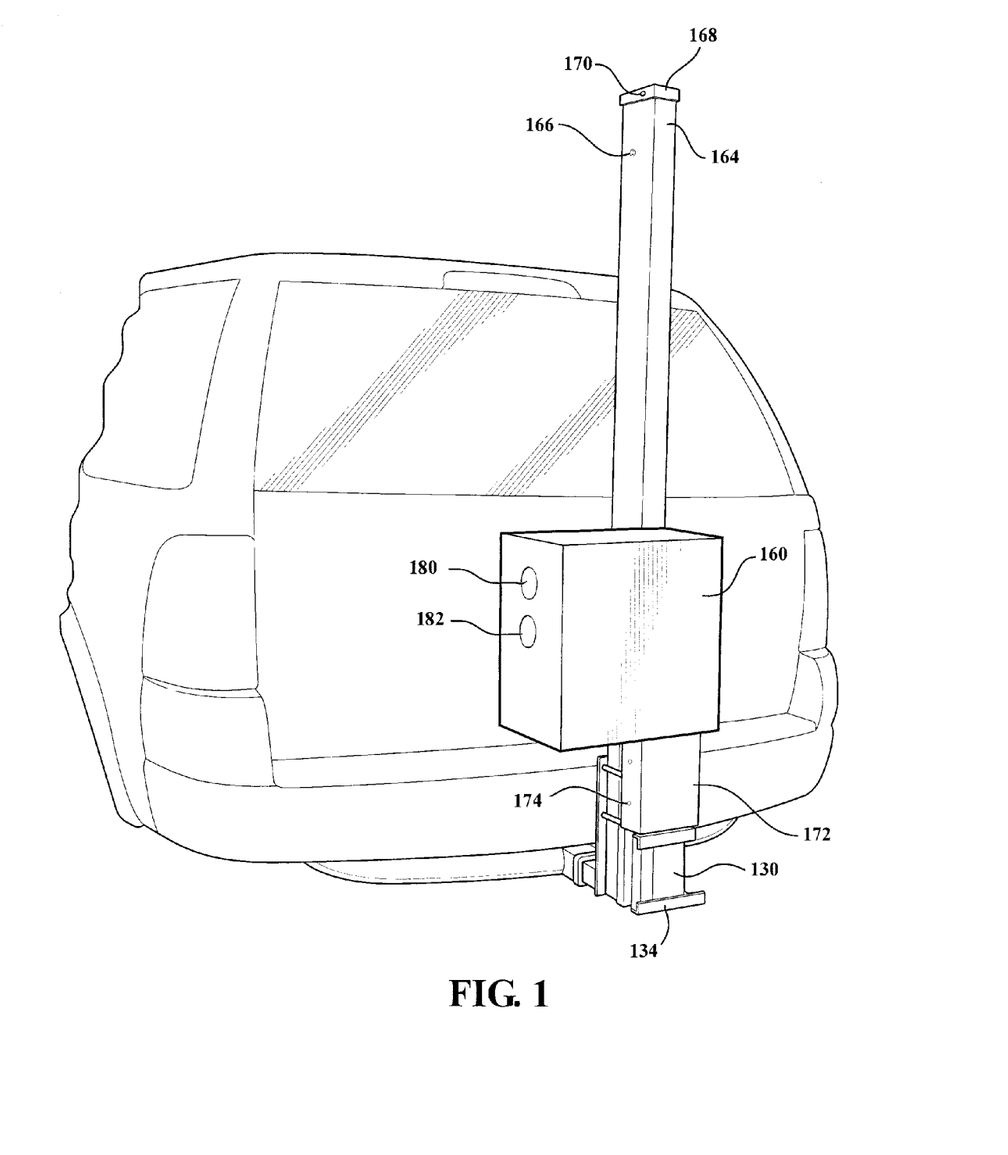
FIG. 1 is a rear view of the soil sampler mounted on a utility vehicle.
Figure 6:
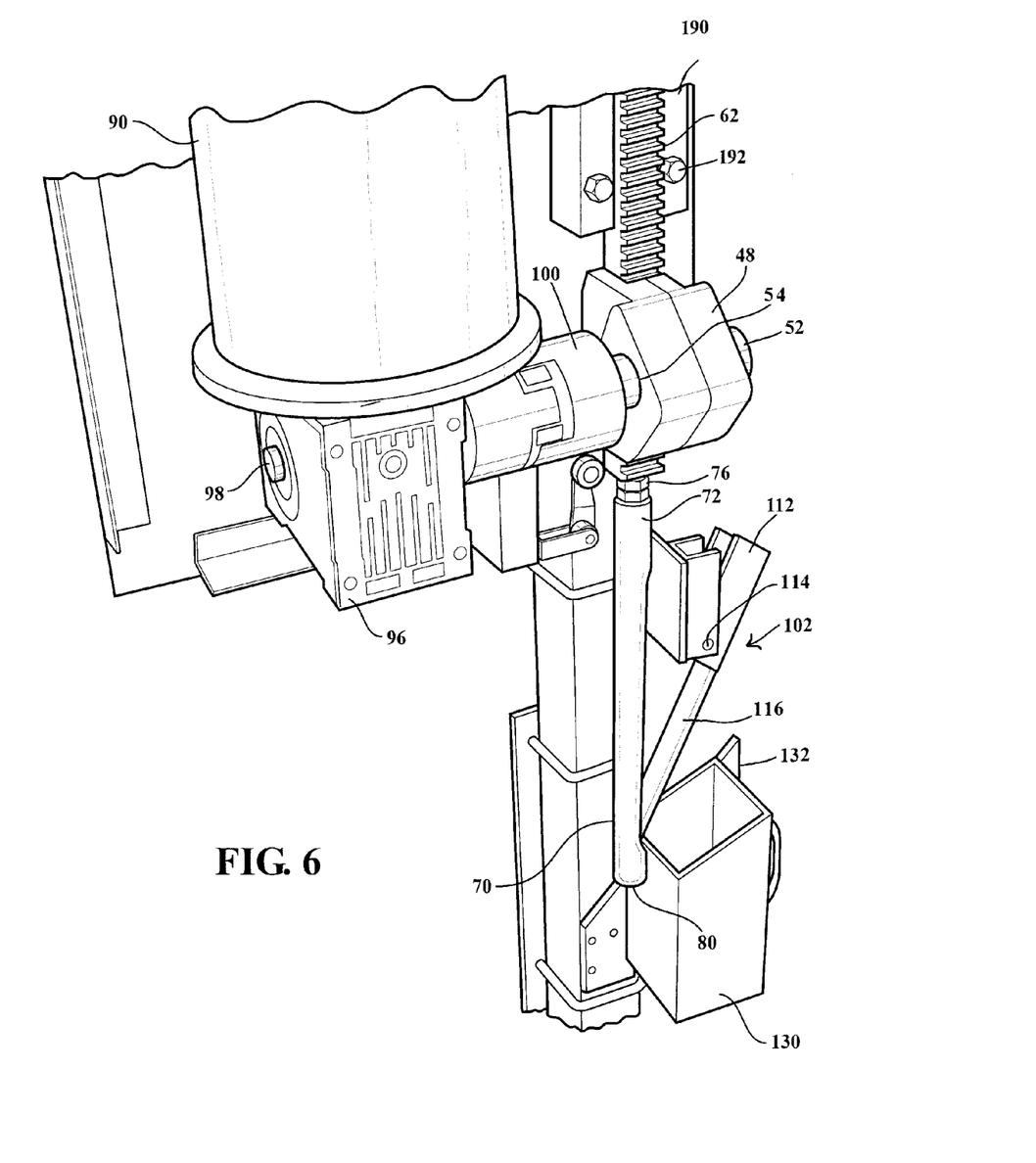
FIG. 6 is a prospective view of the left side and rear of the drive, the soil probe and the spoon assembly.
Figure 7:
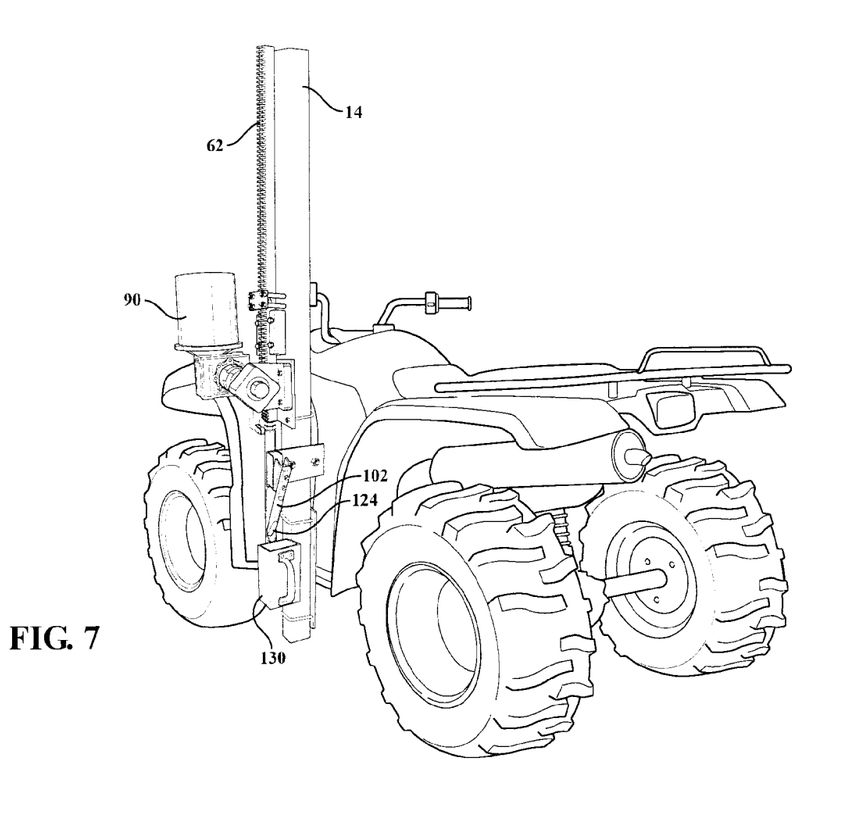
FIG. 7 is a perspective view of the soil sampler, with shields removed and mounted on an all terrain vehicle.

The soil sample container 130 can be mounted on a soil sample container holder 132 shown in FIG. 6. The soil sample container 130 can also be received in a channel provided by a container holder assembly 134 shown in FIG. 1.

The motor support plate 40 carries a lower limit switch 140 with a roller 142 that follows the left side of the elongated steel gear rack 62. A limit switch trigger 144 on the rack 62 is contacted by the roller 142 when the gear rack 62 is in a raised position and turns the electric motor 90 off. An upper limit switch 146, on the motor support plate 40, includes a roller 148 that follows the left side of the gear rack 62. A limit switch trigger 150 on the rack 62 is contacted by the roller 148 when the gear rack 62 is in a selected lowered position. The limit switch trigger 150 controls the depth that the tubular soil probe 70 extends into the soil. The limit switch trigger 150 is adjustable along the length of the gear rack 62 to change the depth of penetration of the tubular soil probe 70. The limit switch trigger 144 on the rack 62 may also be adjustable.

A motor cover 160 encloses the electric motor 90 and the rack drive assembly 46. The motor cover 160 is secured to the motor support plate 40 by fasteners 162. An upper rack cover 164 extends upward from inside the motor cover 160 to the top of the metal tube 14. The upper rack cover 164 is clamped to the metal tube 14 by fasteners 166. A cap 168 covers the top of the tube 14 and the chamber housing the upper portion of the steel gear rack 62. Fasteners 170 fix the cap 168 to the top of the tube 14. A lower rack cover 172 extends downward from the motor cover 160 and the motor support plate 40. The lower rack cover 172 is attached to the metal tube 14 by fasteners 174. Enclosing the motor 90 the rack drive assembly 46 and the steel gear rack 62 protect these assemblies from dust and moisture. Even soil probe 70 is protected when retracted.

The motor cover 160, the upper rack cover 164, the cap 168 and the lower rack cover 172 are removable for maintenance and repair of the soil sampler. An on and off switch 180 and an operator switch 182, shown in FIG. 4, permit an operator to take soil samples with the all three covers attached. The on and off switch 180 permits connecting or disconnecting power to the soil sampler at any time. The operate switch 182 energizes the motor 90, drive the gear rack 62 and the tubular soil probe 70 downward to obtain a soil sample and then return to the raised starting position. As the gear rack 62 and probe 70 return to the raised starting position, the spoon assembly 102 removes the soil sample from the tubular soil probe 70 and the soil sampler 10 is ready to take another soil sample when the operate switch 182 is activated again. If desired the operate switch 182 can be replaced by an up switch and a down switch.

The rack 62 is an elongated steel bar with gear teeth 64 and three machined surfaces. The teeth 64 must remain in vertical alignment relative to the rack drive assembly 46. One or more guide bearings 190 are employed to hold the rack 62 in proper alignment. Each bearing 190 is attached to the motor support plate 40 or to the mast 12 by bolts 192. The bearing 190 as shown in FIGS. 3 and 4 is made from a material such as nylon or an ultra high molecular weight plastic. These bearings 190 have a slot that receives the gear rack 62. The slot in the bearing 190 engages both sides and the flat surface opposite the gear teeth 64. A plate 196 is attached to a plate 40, by bolts 198, and supports a shaft 200. An idler gear 202 is journaled by the shaft 200. The idler gear 202 engages the gear teeth 64 and retains the gear rack 62 in sliding contact with the bearing 190 and the three bearing surfaces.

I claim:

1. A vehicle mounted soil sampler comprising:
    a generally vertical mast;
    a hitch mount assembly adapted to be attached to a vehicle, clamped to said generally vertical mast and wherein the hitch mount assembly is vertically adjustable relative to said generally vertical mast;
    a support plate clamped to said generally vertical mast and vertically adjustable relative to said generally vertical mast;
    a motor connected to a drive shaft and gear journaled in a gear housing, and mounted on the support plate;
    an elongated gear rack with gear teeth, held substantially parallel to said vertical mast by the gear housing and movable parallel to said generally vertical mast, by the motor connected to the drive shaft and gear journaled in the gear housing, in a downward direction and wherein the motor and drive shaft and gear journaled in the gear housing are reversible to move to the elongated gear rack generally parallel to said generally vertical mast in an upward direction;
    a tubular soil probe with an upper end clamped to a bottom end of the elongated gear rack and a soil probe open end which permits movement of soil into the interior of the soil probe upon downward movement of the soil probe by the elongated gear rack, the drive shaft and gear journaled in the gear housing and the motor, and an open slot in the tubular soil probe;
    a spoon bar pivotally attached to a spoon mounting plate, clamped to said generally vertical mast, by a horizontal pivot pin, the spoon bar including a bar lower portion with a concave surface that is movable into and out of the open slot in the tubular soil probe upon pivotable movement about the horizontal pivot pin and a spring urging the lower portion of the spoon bar toward the open slot; and
    a soil sample container supported by said generally vertical mast 12 in a position to catch soil samples moved through the open slot of the tubular soil probe in response to upward movement of the tubular soil probe and the elongated gear rack.

2. A vehicle mounted soil sampler, as set forth in claim 1, wherein the generally vertical mast is a tube with a rectangular cross section.

3. A vehicle mounted soil sampler, as set forth in claim 1, wherein the hitch mount assembly includes a hitch plate clamped to said generally vertical mast, a hitch bar fixed to the hitch plate and extending from the hitch plate and wherein the hitch bar is telescopically receivable in a receiver hitch mounted on said vehicle.

4. A vehicle mounted soil sampler, as set forth in claim 1, wherein the motor is connected to a ninety degree gear box, and a gear box output shaft is connected to the drive shaft and gear journaled in the gear housing by a shaft coupler.

5. A vehicle mounted soil sampler, as set forth in claim 1, wherein the tubular soil probe is held in a fixed position relative to the elongated gear rack to hold the open slot in the tubular soil probe in alignment with the spoon bar.

6. A vehicle mounted soil sampler, as set forth in claim 1, including a handle on the soil sample container.

7. A vehicle mounted soil sampler, as set forth in claim 1, including at least one guide bearing engageable with the elongated gear rack that limits movement of the elongated gear rack away from the drive shaft and gear and is engageable with a first rack side and a second rack side of the elongated gear rack.

8. A vehicle mounted soil sampler, as set forth in claim 7, including an idler gear journaled on the support plate and engageable with the gear teeth of the elongated gear rack and that limits movement of the elongated gear rack from the at least one guide bearing.

9. A vehicle mounted soil sampler, as set forth in claim 1, including a lower limit switch trigger mounted on the elongated gear rack and a lower limit switch that is activated by the lower limit switch trigger to limit upward movement of the elongated gear rack.

10. A vehicle mounted soil sampler, as set forth in claim 9, wherein the lower limit switch trigger is movable to different positions on the elongated gear rack.

11. A vehicle mounted soil sampler, as set forth in claim 1, including an upper limit switch trigger mounted on the elongated gear rack and an upper limit switch that is activated by the upper limit switch trigger to limit downward movement of the elongated gear rack.

12. A vehicle mounted soil sampler, as set forth in claim 11, wherein the upper limit switch trigger is movable to different positions on the elongated gear rack.

13. A vehicle mounted soil sampler comprising:
    a generally vertical mast tube with a rectangular cross section;
    a hitch mount assembly including a hitch plate, clamped to said generally vertical mast tube vertically adjustable relative to said generally vertical mast tube, a hitch bar fixed to the hitch plate and telescopically receivable in a receiver hitch mounted on said vehicle;

a support plate clamped to said generally vertical mast and vertically adjustable relative to said generally vertical mast tube;

a motor connected to a gear box, a gear box output shaft, a shaft coupler and a drive shaft and gear journaled in a gear housing, and wherein the motor and the gear housing are both clamped to the support plate;

an elongated gear rack with gear teeth, held substantially parallel to said generally vertical mast by the gear housing and movable parallel to said generally vertical mast, by the motor connected to the drive shaft and gear journaled in the gear housing, in a downward direction and wherein the motor drive shaft, and gear journaled in the gear housing are reversible to move to the elongated gear rack generally parallel to said generally vertical mast in an upward direction;

at least one rack guide bearing attached to the support plate above the gear housing and engageable with the elongated gear rack to limit movement of the elongated gear rack away from the drive shaft and gear, and engageable with a first rack side and a second rack side;

an idler gear journaled on the support plate and in engagement with the gear teeth of the elongated gear rack adjacent to the at least one guide bearing and above the gear housing, and wherein the idler gear limits movement of the elongated gear rack from the at least one guide bearing;

a tubular soil probe including a probe upper end clamped to a bottom end of the elongated gear rack and a soil probe open end which permits movement of soil into the interior of the soil probe upon downward movement of the soil probe driven by the elongated gear rack, the drive shaft and gear journaled in the gear housing and the motor, and an open slot in the tubular soil probe;

a spoon bar pivotally attached to a spoon mounting plate clamped to said generally vertical mast, by a horizontal pivot pin, the spoon bar including a bar lower portion with a concave surface that is movable into and out of the open slot in the tubular soil probe upon pivotable movement about the horizontal pivot pin and a spring urging the bar lower portion of the spoon bar toward the open slot; and a soil sample container supported by said generally vertical mast in a position to catch soil samples moved through the open slot of the tubular soil probe in response to upward movement of the tubular soil probe and the elongated gear rack.

14. A vehicle mounted soil sampler, as set forth in claim 13, including an upper lock nut on a threaded stud that engages an elongated gear rack bottom end and holds the upper lock nut and the threaded stud from rotating relative to the elongated gear rack; and a lower lock nut on the threaded stud that engages the tubular soil probe, after the tubular soil probe is screwed onto the threaded stud, and holds the tubular soil probe in a selected position with the open slot in the tubular soil probe in position to receive the bar lower portion of the spoon bar.

15. A vehicle mounted soil sampler, as set forth in claim 13, including a lower limit switch trigger mounted on the elongated gear rack a lower limit switch that is activated by the lower limit switch trigger to limit upward movement of the elongated gear rack.

16. A vehicle mounted soil sampler, as set forth in claim 13, including an upper limit switch trigger mounted on the elongated gear rack and an upper limit switch that is activated by the upper limit switch trigger to limit downward movement of the elongated gear rack.

17. A vehicle mounted soil sampler, as set forth in claim 16, wherein the upper limit switch trigger is movable to different positions on the elongated gear rack to adjust the depth of soil penetration by the tubular soil probe.

18. A method of adjusting a vehicle mounted soil sampler comprising:

clamping a hitch mount assembly to a generally vertical mast in a position that accommodates the height of a receiver hitch mounted on said vehicle;

clamping a motor support plate to said generally vertical mast in a position which provides a desired space between a tubular soil probe and the ground when the tubular soil probe is in a raised position;

clamping a spoon mounting plate to said generally vertical mast in a selected position in which a lower portion of a spoon bar is a selected distance above a bottom of a slot in the tubular soil probe and the tubular soil probe is in the raised position; and mounting an upper limit switch trigger on a selected position on an elongated gear rack that provides the desired depth of soil penetration by the tubular soil probe.

* * * * *